United States Patent [19]

Hiltebrandt et al.

[11] 4,060,087
[45] Nov. 29, 1977

[54] SINGLE OR DOUBLE-SHANK CUTTING LOOP DEVICE FOR RESECTOSCOPES

[75] Inventors: Siegfried Hiltebrandt; Ludwig Bonnet, both of Knittlingen, Germany

[73] Assignee: Richard Wolf GmbH, Knittlingen, Germany

[21] Appl. No.: 694,990

[22] Filed: June 11, 1976

[30] Foreign Application Priority Data

June 11, 1975 Germany .............................. 2525982

[51] Int. Cl.² ............................................ A61B 17/32
[52] U.S. Cl. .............................................. 128/303.15
[58] Field of Search ...................... 128/303.15, 303.13, 128/303.14, 303.16, 303.17

[56] References Cited

U.S. PATENT DOCUMENTS

| 1,794,296 | 2/1931 | Hyams | 128/303.14 |
| 2,011,169 | 8/1935 | Wappler | 128/303.15 |
| 3,149,633 | 9/1964 | Zingale | 128/303.15 |
| 3,856,015 | 12/1974 | Iglesias | 128/303.15 |
| 3,901,242 | 8/1975 | Storz | 128/303.15 |

FOREIGN PATENT DOCUMENTS 2,324,658   12/1974   Germany ........................ 128/303.17

Primary Examiner—John D. Yasko
Assistant Examiner—Lee S. Cohen
Attorney, Agent, or Firm—Kinzer, Plyer, Dorn & McEachran

[57] ABSTRACT

A cutting loop device for a resectoscope comprising two arms carrying two parallel cutting loops of wire in the distal end region of the device, the more proximal of said cutting loops being connectable via one of said arms to the live pole of a high frequency current source and the more distal of said cutting loops being connectable via the other of said arms to the neutral pole of said source.

5 Claims, 4 Drawing Figures

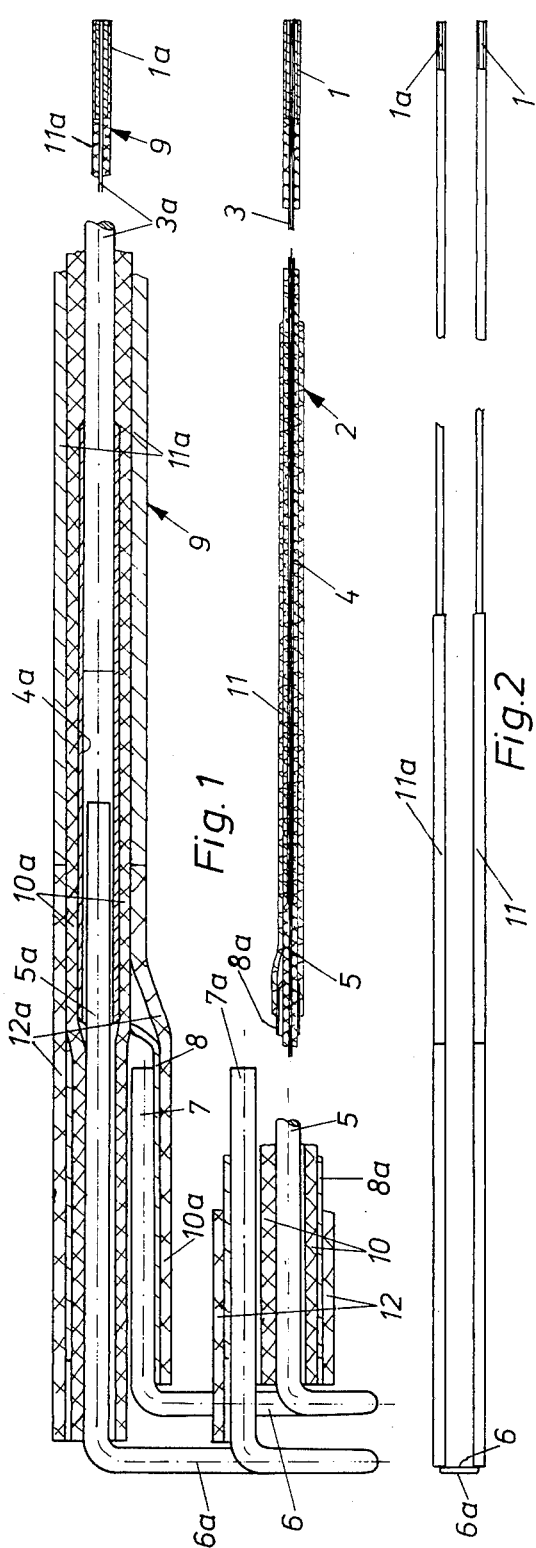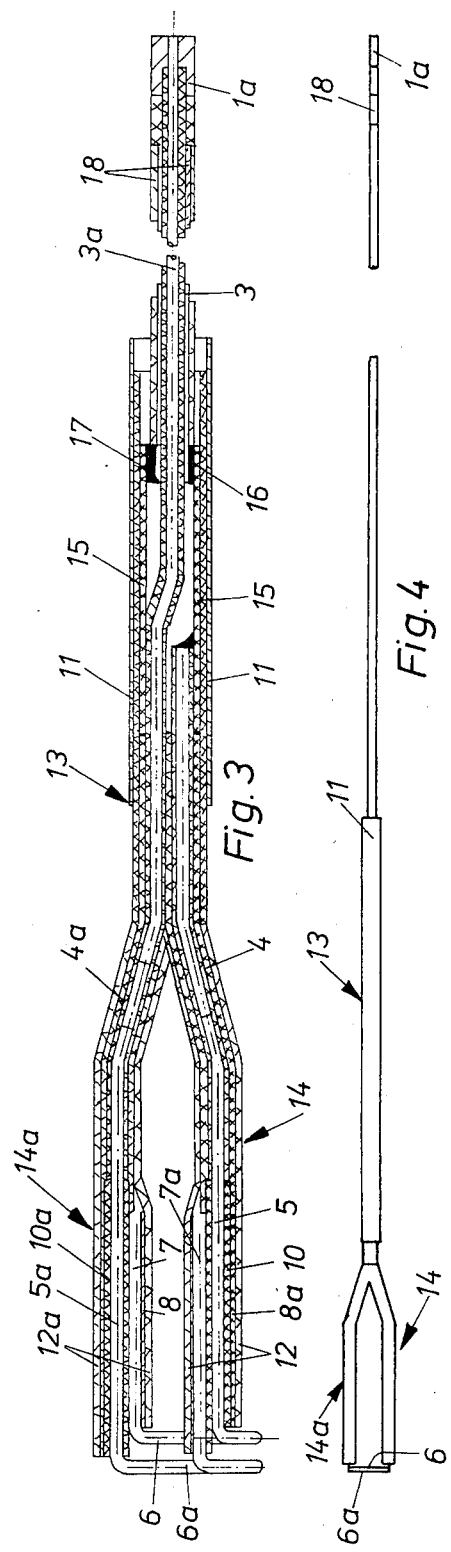

SINGLE OR DOUBLE-SHANK CUTTING LOOP DEVICE FOR RESECTOSCOPES

BACKGROUND OF THE INVENTION

1. Field of the Invention

The invention relates to a double-shank cutting loop, or a single-shank loop which extends at the distal end into a fork, which cutting loop can be supplied with high frequency current and is intended for resectoscopes whose cutting loop is curved in a semicircle and lies in, or approximately in, a plane perpendicular to the longitudinal direction.

2. Description of the Prior Art

Hitherto single-pole cutting loops have been used in resectoscopy for removing prostate adenomas. These loops are supplied with HF current in a co-called electrotome over which the outer barrel is fitted, and are connected to the live pole of an HF generator, while the neutral pole of the HF circuit is applied to the patient's body over an area thereof. By moving the hairpin shaped cutting loop in the proximal direction the prostate adenoma is cut away in strips. With such single-pole cutting loops, mishaps may result in the unintentional and uncontrollable capacitive transmission of current to the outer barrel and thus to damage to the mucous membrane of the urinary passage, which then results in strictures in the passage. When the resectoscope is inserted, lubricants are used which form an insulating film between the outer barrel and the walls of the urinary passage but in the event of high HF currents being transmitted capacitively this film breaks down, which results in unintended coagulations which after a time also lead to strictures in the passage.

The main object of the present invention is to prevent the said capacitive transmission of uncontrollable HF currents when prostate resection is performed using cutting loops powered by HF current.

SUMMARY OF THE INVENTION

To this end the invention consists in a cutting loop for resectoscopes, comprising two parallel loops of wire of which the more proximal loop can be coupled via one shank or one form-arm to the live pole of an HF circuit and of which the more distal loop can be coupled via the other shank or fork-arm to the neutral pole of the circuit.

In this way it is possible to bring both poles of the high frequency current up to the tissue to be removed from the prostate without the possibility of uncontrollable currents being transmitted, it being essential that the live pole of the HF circuit should in all cases be connected to that loop which is nearer the proximal end of the resectoscope (i.e. nearer the eye of the doctor performing the operation) so that the prostate adenoma can be removed in the cutting i.e. distal to proximal, direction while under observation.

The distance between the two parallel loops of wire may vary between approximately 0.3 and approximately 2mm to suit the HF voltage. The coagulating current transmitted between the more proximal loop of wire and the more distal loop of wire is precisely fixed under all circumstances and thus any possibility of tissue being coagulated when not intended is excluded.

BRIEF DESCRIPTION OF THE DRAWINGS

FIG. 1 is an interrupted longitudinal section through a bi-polar double-shank cutting loop for a resectoscope with the distal parts of the shanks shown enlarged, FIG. 2 is an actual size plan view of the cutting loop of FIG. 1, FIG. 3 is an interrupted longitudinal section through a single shank bi-polar cutting loop to an enlarged scale.

FIG. 4 is an actual size plan view of the cutting loop of FIG. 3.

DESCRIPTION OF THE PREFERRED EMBODIMENT

In FIGS. 1 and 3 the wire loops of the cutter electrodes are turned or canted slightly in comparison with FIGS. 2 and 4 for greater clarity.

In the case of the double-shank cutter electrode shown in FIGS. 1 and 2, a threaded proximal part 1, which acts as a connecting contact for one shank 2 of the shanks, continues into an active HF conductor 3 (of copper wire for example) which is soldered into one end of a conductive tube 4 into whose other end is soldered a loop 5 of wire (e.g. a loop of special tungsten wire). At the distal end the loop 5 is curved into a semicircular loop 6 in a plane perpendicular to the longitudinal direction and its free end 7 is mounted distally in a metal sleeve 8 in the other shank 9.

The configuration of the shank 9 which is to be connected to the neutral pole of the HF source is the same as that of the shank 2 containing the active conductor 3, but similar parts bearings the same reference numerals are given an added "a" in the case of the former in all cases the neutral loop 6a is situated further forward in the distal direction than the live loop 6.

Depending on the HF voltage, the distance between the two parallel, semicircular loops of wire 6, 6a, whose radius of curvature is the same, may be from approximately 0.3 to approximately 2m and it may be set by means of insulating distance pieces. The current conductors 3, 3a, the straight portions 5, 5a of the loops of wire and the tubes 4, 4a are enclosed in respective insulating sheaths 10, 10a of high dielectric strength and the sheaths terminate at the distal end of the instrument immediately before their respective loops 6, 6a. Depending on the kind of resectoscope, a conductive metal tube 11, 11a may be drawn over the sheath, this tube continuing at the distal end into an insulating sheath piece 12, 12a which surrounds the metal sleeve 8, 8a.

In the case of the single-shank embodiment shown in FIGS. 3 and 4, the shank 13 extends at the distal end into the arms 14, 14a of a fork. Arm 14 of the fork holds the straight part 5 of the live loop of wire 6, of which the free end 7 is mounted in the same way as was described with reference to FIGS. 1 and 2 in the other arm 14a of the fork. Arm 14a of the fork holds the straight part 5a of the neutral, distally more advanced loop 6a whose free end 7a is mounted in fork arm 14. In the present case the proximal ends of the straight parts 5 and 5a of the loops are soldered into conductive metal tubes 4, 4a which are insulated from one another. Tube 4 is soldered into a metal bush 15, which is soldered at 16 to the conductive wire 3 via an eccentric ring 17. Wire 3 is joined to an annular contact 18 which is connected to the live pole of the HF source. The neutral, insulated conductive wire 3a is soldered at the proximal end into tube 4a and is connected at the proximal end to a contact 1a which is able to be coupled to the neutral pole of the HF source.

In this case, too, the wire loop 6 which is to be connected to the live pole of the HF source must lie farther forward in the proximal direction than the wire loop 6a which is to be connected to the neutral pole, and once again the two parallel semicircular loops of wire, whose radius of curvature is the same are spaced a specific distance apart as was described with reference to FIGS. 1 and 2. Also, in the case of the embodiment shown in FIGS. 3 and 4 there is provided on the proximal side of the fork arm 14, 14a, a metal tube 11, oval in the present case, which is flattened on one side and which acts as a guide and to counteract rotation in the resectoscope.

It is understood that in the case of the embodiment shown in FIGS. 3 and 4 it is also possible for the more proximal loop of wire 6 to be connected to contact 1a, which would then have to be connected to the live pole of the HF source, while the annular contact 18, which would have to be connected to the neutral pole, would then be connected to the more distal loop of wire 6a.

We claim:
1. An electrical surgical instrument for resection, comprising:
   a. shank means having a proximal and a distal end and comprising two arms each having insulation along the length thereof,
   b. two parallel wires respectively carried in the insulation and terminating in two parallel single cutting loops of wire supported by said arms at the distal end of the shant means, remote from the surgeon, said cutting loops lying respectively in planes spaced a predetermined distance from each other normal to the axis of the shank means and
   c. means for connecting said cutting loops to a high frequency current source, including;
      i. two conductors, each connected to a respective one of said cutting loops and passing through a respective one of said arms, and
      ii. two conductive contacts carried by said shank means at the opposite proximal end thereof, and each connected to a respective one of said conductors, whereby the more proximal of said cutting loops can be connected to the live pole of said high frequency source and the more distal of said cutting loops can be connected to the neutral pole of said source.

2. An electrical surgical instrument as claimed in claim 1, wherein said shank means is in the form of a double shank of which the two individual shanks comprise said two arms respectively.

3. An electrical surgical instrument as claimed in claim 1, wherein said shank means is in the form of a single shank and said arms are the arms of a fork which is continuous with said single shank.

4. An electrical surgical instrument as claimed in claim 1, wherein the two parallel cutting loops of wire are spaced apart by a distance of from approximately 0.3mm to approximately 3mm depending on the high frequency voltage.

5. An electrical surgical instrument as claimed in claim 1, wherein said cutting loops consist of tungsten wire, and wherein said conductors each include a conductive tube connected to a respective one of said cutting loops and a lead connecting said tube to a respective one of said contacts.

* * * * *